(12) United States Patent
Yandell et al.

(10) Patent No.: US 11,388,912 B2
(45) Date of Patent: Jul. 19, 2022

(54) METHODS TO LOWER OIL CONTENT IN DISTILLERS GRAINS

(71) Applicant: Buckman Laboratories International, Inc., Memphis, TN (US)

(72) Inventors: Eric Yandell, West Lafayette, IN (US); Dimitri Kuznetsov, Memphis, TN (US); Mahesh Budhathoki, Memphis, TN (US); Chamindu Liyanapatirana, Memphis, TN (US)

(73) Assignee: BUCKMAN LABORATORIES INTERNATIONAL, INC., Memphis, TN (US)

( * ) Notice: Subject to any disclaimer, the term of this patent is extended or adjusted under 35 U.S.C. 154(b) by 587 days.

(21) Appl. No.: 16/195,876

(22) Filed: Nov. 20, 2018

(65) Prior Publication Data

US 2019/0159479 A1 May 30, 2019

Related U.S. Application Data

(60) Provisional application No. 62/591,222, filed on Nov. 28, 2017.

(51) Int. Cl.
*A23K 10/38* (2016.01)
*B01D 21/26* (2006.01)
(Continued)

(52) U.S. Cl.
CPC ............ *A23K 10/38* (2016.05); *B01D 21/262* (2013.01); *C11B 1/00* (2013.01); *C11B 1/10* (2013.01);
(Continued)

(58) Field of Classification Search
CPC .......... A23K 10/38; B01D 21/262; C12F 3/10
(Continued)

(56) References Cited

U.S. PATENT DOCUMENTS 3,301,881 A 1/1967 Davis
5,250,182 A 10/1993 Bento et al.
(Continued)

FOREIGN PATENT DOCUMENTS

WO 2016201209 A1 12/2016

OTHER PUBLICATIONS

International Search Report and Written Opinion issued in corresponding International Patent Application No. PCT/US2018/061901 dated Feb. 12, 2019 (17 pages).
(Continued)

*Primary Examiner* — Katherine D Leblanc
(74) *Attorney, Agent, or Firm* — Kilyk & Bowersox, P.L.L.C.

(57) ABSTRACT

A method and system for improving ethanol production from biomass are provided which includes adding at least one separation aid to stillage, that is preferably whole stillage, that contains oil and/or fat generally in the form of an emulsion, to form a treated stillage prior to centrifuging the stillage, and centrifuging the treated stillage in at least one centrifuge to separate at least a portion of the solids content from the treated stillage. The separation aid contains at least one anionic surfactant, at least one non-ionic surfactant, at least one organic solvent that is miscible in water, and water, and optionally at least one lecithin. Treated stillage products are also provided which can contain the indicated separation aid.

30 Claims, 1 Drawing Sheet

(51) Int. Cl.
   *C12F 3/10* (2006.01)
   *C11B 1/00* (2006.01)
   *C11B 1/10* (2006.01)
   *C12P 7/08* (2006.01)
   *C12F 3/00* (2006.01)
   *C11B 13/00* (2006.01)
   *C12F 3/08* (2006.01)

(52) U.S. Cl.
   CPC ............... *C11B 13/00* (2013.01); *C12F 3/00* (2013.01); *C12F 3/08* (2013.01); *C12F 3/10* (2013.01); *C12P 7/08* (2013.01)

(58) Field of Classification Search
   USPC ...................................................... 426/442
   See application file for complete search history.

(56) References Cited

U.S. PATENT DOCUMENTS

| | | |
|---|---|---|
| 6,403,344 B1 | 6/2002 | Marellapudi et al. |
| 8,962,059 B1 | 2/2015 | Froderman et al. |
| 9,328,311 B2 | 5/2016 | Jenkins et al. |
| 2009/0209664 A1* | 8/2009 | Talingting-Pabalan ............... B01D 17/047 514/785 |
| 2012/0125859 A1 | 5/2012 | Collins et al. |
| 2016/0115425 A1 | 4/2016 | Blankenburg et al. |

OTHER PUBLICATIONS

Salager et al. "How to Attain an Ultralow Interfacial Tension and a Three-Phase Behavior with a Surfactant Formulation for Enhanced Oil Recovery: A Review. Part 2. Performance Improvement Trends from Winsor's Premise to Currently Proposed Inter- and Intra-Molecular Mixtures," Journal of Surfactants and Detergents, 2013, vol. 16, No. 5, pp. 631-663.

Diaz-Royon et al., "Composition of Fat in Distillers Grains," Iowa State University Digital Repository, 2012, pp. 1-9 (11 pages).

Salager., "Surfactants Types and Uses," Universidad de Lod Andes, FIRP Booklet #E300-A, 2002, Version # 2 (50 pages).

\* cited by examiner

METHODS TO LOWER OIL CONTENT IN DISTILLERS GRAINS

This application claims the benefit under 35 U.S.C. § 119(e) of prior U.S. Provisional Patent Application No. 62/591,222, filed Nov. 28, 2017, which is incorporated in its entirety by reference herein.

FIELD OF THE INVENTION

The present invention relates to methods and systems used in ethanol production from biomass. More specifically, the present invention relates to a separation aid that can be used in the production of wet cake, distillers grains (DG), and/or distillers dried grains & solubles (DDGS).

BACKGROUND OF THE INVENTION

Ethanol production from biomass has received significant attention in recent years as a source of alternative fuel or biofuel or an oxygenating additive to conventional gasolines. Ethanol burns more cleanly than fossil fuels, reduces carbon monoxide emissions when used in gasoline blends, and can be produced using renewable resources such as grains or other renewable starch-containing biomass. A widely used method of producing ethanol from grains is known as "dry milling" and usually is practiced using corn in the United States. The dry milling process usually uses the starch in the corn or other renewable biomass to produce ethanol through fermentation, which creates a resulting stream comprised of byproducts termed "whole stillage." Whole stillage may be further separated by centrifuge. The separation produces a heavy fraction containing most of the suspended solids, known as "wet distillers grains" (WDG) and produces a light fraction containing most of the dissolved solids and emulsified oil, known as "thin stillage." Wet distillers grains contains significant amounts of oil which is not recovered and leaves the process at this point.

Both wet distillers grains and thin stillage contain valuable oil, protein, and fiber, and are used primarily to supplement animal feed, mostly in the form of distillers dried grains with solubles (DDGS). DDGS typically is produced by evaporating the thin stillage (to recover and return water back into the process), separating the oil, recombining the remainder with wet distillers grains, and finally drying the product to have a low moisture content. Oil contained in the evaporated thin stillage can be removed as a standalone shippable product using numerous methods known to those skilled in the art. The remainder, also known as defatted syrup, typically contains a negligible amount of oil.

A valuable byproduct of the above described ethanol production process is using distillers grains in animal feed or as at least a portion of animal feed. However, high oil contents in distillers grains is undesirable and believed to contribute to a decrease milk production in dairy cows and increased pork bellies in swine. Oil contents of about 6 wt % to 7 wt % or lower in distillers grains on a dry basis are preferred by the animal feed industry.

The present inventors have recognized that there is a need for a more efficient and better method to reduce oil content in distillers grains for at least the reasons provided above.

SUMMARY OF THE PRESENT INVENTION

A feature of the present invention is to provide a method of producing wet distillers grains (WDG), dry distillers grain (DDG), or DDGS with less oil content.

A further feature of the present invention is to provide a method so that whole stillage can be treated prior to a centrifuging step to increase the oil content of thin stillage and obtain WDG, DDG, and/or DDGS with a lower oil content.

Another feature of the present invention is to provide a separation aid that increases the rate of drainage of suspended solids and/or dislodges emulsified, trapped, and/or attached oil and fats from wet distillers grains (as part of the whole stillage) during centrifugation.

A further feature of the present invention is to provide a system with interoperable equipment to supply and apply the indicated separation aid that is useful for decreasing the oil and fats content of suspended solids separated from stillage or other biomass, and optionally a separating unit for recovering suspended solids from the treated biomass.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates, in part, to a method to lower oil content in distillers grains from a fermentation process. The method includes adding at least one separation aid to stillage that contains suspended solids as well as oil generally in the form of an oil emulsion, to form a treated stillage prior to centrifuging the stillage, and then centrifuging the treated stillage in at least one centrifuge to separate a heavy fraction containing mostly of solids (e.g., wet cake or WDG) from a light fraction containing mostly liquid (e.g., thin stillage) and including at least a portion of the oil emulsion from said treated stillage. The separation aid of the present invention is not intended to break oil and fats from the light fraction into a continuous phase, but merely dislodges them from the heavy fraction so that they are carried downstream where they can be removed as a standalone stream using conventional methods known to those skilled in the art. The separation aid preferably includes at least one anionic surfactant, at least one non-ionic surfactant, at least one organic solvent that is miscible in water, and water, and optionally at least one lecithin. For instance, the separation aid can be or include a) at least one sulfocarboxylate, sulfated alcohol, or sulfated alcohol ethoxylate, b) ethoxylated castor oil, c) propylene glycol, and d) water. As another example, the separation aid can be or include a) at least one sulfocarboxylate, sulfated alcohol, or sulfated alcohol ethoxylate, b) ethoxylated castor oil, c) propylene glycol, d) water, and e) at least one alcohol.

In yet a further example, the separation aid can be or include a) at least one sulfocarboxylate, sulfated alcohol, or sulfated alcohol ethoxylate, b) ethoxylated castor oil, c) propylene glycol, d) water, e) at least one alcohol, and f) at least one lecithin.

The present invention further relates to methods to reduce the oil content in wet cake, WDG, DDG, and/or DDGS by utilizing the present invention.

The present invention also relates to a separation aid or composition that can be or includes at least one anionic surfactant, at least one non-ionic surfactant, at least one organic solvent that is miscible in water, and water, and optionally at least one lecithin. The separation aid is generally present or formulated as an entirely liquid formulation (at 25° C.). For example, the separation aid or composition can be or include from about 5 wt % to about 40 wt % of at least one sulfocarboxylate, sulfated alcohol, or sulfated alcohol ethoxylate, from about 1 wt % to about 25 wt % ethoxylated castor oil, from about 5 wt % to about 25 wt % propylene glycol, from 1 wt % to about 15 wt % alcohol (e.g., ethyl alcohol), and from about 10 wt % to about 75 wt % water (based on the total weight of the composition). As a further example, the separation aid or composition can be or include from about 5 wt % to about 40 wt % of at least one sulfocarboxylate, sulfated alcohol, or sulfated alcohol ethoxylate, from about 1 wt % to about 25 wt % ethoxylated castor oil, from about 5 wt % to about 25 wt % propylene glycol, from 1 wt % to about 15 wt % alcohol (e.g., ethyl alcohol), from about 10 wt % to about 75 wt % water, and from about 5 wt % to about 20 wt % of at least one lecithin (based on the total weight of the composition).

The present invention also relates to a treated stillage, such as treated whole stillage that includes a) the separation aid or composition and b) stillage, wherein the separation aid can be present in an amount of from about 10 ppm to about 1,000 ppm.

The present invention also relates to a wet cake, WDG, DDG, and/or DDGS recovery system, comprising a supply of biomass that comprises stillage, such as whole stillage; a supply of the indicated separation aid; a treatment unit for combining the separation aid with the biomass to form treated biomass; and a centrifuge for separating at least a portion (e.g., a majority, over 60 wt %, over 70 wt %, over 80 wt %, over 90 wt %, over 95 wt %, up to 99.9 wt % of oil emulsion present) of the liquid oil emulsion from the treated biomass to produce wet cake, WDG, DDG, and/or DDGS with a lower oil content.

As used herein, "wet cake," "wet distillers grains," "dried distillers grains," "dried distillers grains with solids" refers to the solids fraction of the stillage with various moisture contents that are separated from their suspension using density based separation, particularly centrifugal separation.

As used herein, "bio-oil" refers to food-grade and non-food grade oils and fats that are derived from plants and/or animals (e.g., vegetable oils and animal fats) or from biomass, which contain primarily triglycerides, but can also contain fatty acids, diglycerides and monoglycerides. As used herein, the term "fat" is understood to include "lipids." Examples of bio-oils derived from plants include, but are not limited to, corn oil, sorghum (milo) oil, wheat oil, soybean oil, sugarcane oil, sunflower oil, flaxseed oil, canola oil, and the like. Other bio-oils include algaculture bio-oils (from algae).

As used herein, "biofuel" refers to any renewable solid, liquid or gaseous fuel produced biologically, such as bio-oils, including for example, bio-oils derived from biomass. Biofuels also include, but are not limited to, biodiesels, bioethanol (i.e., ethanol), biogasoline, biomethanol, biobutanol, and the like.

As used herein, "biomass" refers generally to organic matter harvested or collected from a renewable biological resource as a source of energy. The biomass or biomass material can benefit from the processes of the present invention. The renewable biological resource can include plant materials (e.g., plant biomass), animal materials, and/or materials produced biologically. Biomass includes plant or animal matter that can be converted to biofuels. The biomass can be grown from numerous types of plants and trees, including, but not limited to, annual agricultural crops, starch based plants, sugar based plants, *miscanthus*, switch-grass, hemp, corn, beets, poplar, willow, sorghum, soybeans, wheat, sugarcane, bamboo, and/or a variety of tree species, ranging from *eucalyptus* to oil palm (palm oil). Also, residue from annual crops or harvesting of annual crops or from trees or residue from trees or harvesting of trees or other plant materials (e.g. including stalks, leaves, chaff, husks and the like) and/or perennial plants can be biomass and be used in the methods of the present invention. The term "biomass" is not considered to include non-renewable fossil fuels, such as coal, petroleum and natural gas, which do not normally include glycerides (e.g., tri-, di-, mono-).

As used herein, "stillage" refers to a co-product or byproduct produced during production of a biofuel. The stillage can result from the processing of one or more of the biomass mentioned herein. When used without qualification, the term "stillage" can refer to whole stillage, thin stillage, or concentrated stillage such as condensed distillers soluble, i.e., syrup, which can be produced from biofuel process streams, e.g., bioethanol production process streams. The differences between these different forms of stillage can be further understood with reference to FIG. 1 herein. The stillage can be a byproduct from a corn fermentation process or a byproduct from a sugar cane fermentation process.

As used herein, a "centrifuge" is a piece of equipment, generally driven by a motor that can put a mixture, blend or slurry in rotation around a fixed axis, applying a force perpendicular to the axis. Centripetal acceleration generated in the centrifuge causes denser and lighter substances of the mixture, blend or slurry to separate out. Centrifuges can be oriented horizontally, vertically, or other orientations.

As used herein, the term "oil" being removed from the stillage includes fats in the stillage, wherein some or many or all of these fats are liquified at the temperatures at which the methods of the present invention are operated at. Fats generally are considered oils that are solids at room temperature (or 25° C.).

As used herein, an "evaporator" is a device used to evaporate or vaporize the liquid form of a chemical or chemicals in a mixture, blend or slurry into gaseous or vapor form. The evaporation of more volatile components of a mixture, blend or slurry in an evaporator can concentrate the remaining less volatile liquid components in the device.

As used herein, "surfactant" refers to a compound that can lower the surface tension of a liquid, the interfacial tension between two liquids, or that between a liquid and a solid.

As used herein, an "anionic surfactant" is an organic compound that has a charged group at either terminal end group thereof, wherein the organic compound can lower the surface tension of a liquid, the interfacial tension between two liquids, or that between a liquid and a solid.

As used herein, a "non-ionic surfactant" is an organic compound that is amphiphilic and has no charge group at either terminal end group thereof, wherein the organic compound can lower the surface tension of a liquid, the interfacial tension between two liquids, or that between a liquid and a solid.

It is to be understood that both the foregoing general description and the following detailed description are exemplary and explanatory only and are intended to provide a further explanation of the present invention, as claimed.

The accompanying drawings, which are incorporated in and constitute a part of this application, illustrate some of the features of the present invention and together with the description, serve to explain the principles of the present invention.

DETAILED DESCRIPTION OF THE PRESENT INVENTION

The present invention provides a method to be utilized in ethanol production. The method has the ability to lower oil content (and/or fat content) in distillers grains (e.g., WDG or DDG or DDGS) resulting from a fermentation process. Lowering the oil content of distillers grains can be beneficial since lower oil is desired when distillers grains, for instance, is used in animal feed. Also, a better separation process from the stillage, such as the whole stillage, permits higher oil and fats recovery for bio-oil production as a standalone product.

In the present invention, the method involves adding at least one separation aid to stillage (e.g. whole stillage) that contains emulsified oil (e.g., that can include 'fats'), to form a treated stillage prior to centrifuging the stillage. The method then involves centrifuging the treated stillage in at least one centrifuge to separate at least a portion of the liquid phase from the treated stillage to obtain wet cake or wet distillers' grain and then dried distillers' grain. The step of centrifuging the treated stillage can be done once, twice, or three or more times in at least one centrifuge to separate at least a portion of the suspended solids (e.g., remove at least 0.1 wt % to 100 wt % or 25 wt % to 100 wt %, or 50 wt % to 100 wt %, or 75 wt % to 100 wt %, or 85 wt % or more of available suspended solids present in the treated stillage based on the weight of suspended solids present in treated stillage) from the treated stillage.

As more specific examples, the present invention includes adding at least one separation aid to whole stillage from an ethanol fermentation process, and centrifuging at least once, this treated whole stillage to separate and obtain wet cake or WDG (high solids content) and thin stillage (high liquid content) and separating the wet cake or WDG from the thin stillage, wherein the separation aid has promoted, increased, or otherwise caused more of the oil in the whole stillage to be in the thin stillage fraction and not in the wet cake or WDG. This is in part due to the ability of the separation aid to solubilizing and/or wetting the oil present in the whole stillage so that the oil separates more easily from the wet cake or WDG parts of the whole stillage and becomes part of the thin stillage fraction of the whole stillage upon centrifuging and separation. In one aspect, the separation aid of the present invention is not an emulsion breaker and/or does not function as an emulsion breaker. In the present invention, the oil present in the whole stillage is essentially in the form of an oil emulsion (e.g., oil-in-water emulsion) and the separation aid maintains this emulsion form during treatment and for separating the oil in this form during centrifuging. In one aspect, the separation aid is a non-oil breaker. The separation aid in one aspect, has the ability to improve wettability so that more of the emulsion separates from the solid fraction. In one aspect, the separation aid causes or promotes easier separation or more separation of the oil emulsion from the solid by reducing the interfacial tension of the oil emulsion.

In the present invention, the separation aid can be, include, comprise, consists essentially of, or consists of at least one anionic surfactant, at least one non-ionic surfactant, at least one organic solvent that is miscible in water, and water, and optionally at least one lecithin.

In the present invention, the fermentation process can comprise, consists essentially of, include, or consists of fermentation of the biomass, distillation of the fermented product, and the recovery of ethanol and the separate recovery of whole stillage. The whole stillage can be subjected to one or more centrifuges to separate coarse suspended solids from thin stillage, wherein the thin stillage can be subjected to a series of evaporators that the stillage can enter sequentially. The coarse suspended solids can be considered or ultimately become the wet cake or the wet distillers grains (WDG) and then the dry distillers grains (DDG) after drying. The adding of the separation aid can be to the whole stillage or to at least a portion of the whole stillage, but prior to any centrifuging of the whole stillage.

The separation aid and one, more than one, or all of the components that form the separation aid of the present invention can meet required criteria for animal feed regulations. For example, the components that form the separation aid are preferably listed as GRAS approved products and individually are commonly found in many food applications. As some of its advantages, the separation aid can comprise GRAS approved starting materials, can be used at lower dosage requirements with improved separation of wet cake and/or with decreased centrifuge fouling and improved post separation.

In the present invention, the separation aid can be, includes, comprises, consists essentially of, or consists of at least one anionic surfactant, at least one non-ionic surfactant, at least one organic solvent that is miscible in water, and water, and optionally at least one lecithin.

Regarding the anionic surfactant, the anionic surfactant can be a sulfocarboxylate, sulfate, sulfonate, phosphate, or carboxylate (e.g., ester or ether carboxylate). More specific examples are sulfocarboxylates, alkyl sulfates, alkane sulfonates, alkyl aryl sulfonates, phosphate esters, carboxylate esters or ethers. Examples include, but are not limited to, an alkyl sulfosuccinate such as a dioctyl sulfosuccinate (e.g., a sodium dioctyl sulfosuccinate). Other suitable alkyl sulfosuccinates include sodium dihexyl sulfosuccinate, sodium dicyclohexyl sulfosuccinate, disodium isodecyl sulfosuccinate and the like. Other examples are alkyl sulfates, such as ammonium lauryl sulfate, sodium lauryl sulfate (sodium dodecyl sulfate, SLS, or SDS), or other alkyl-ether sulfates sodium laureth sulfate (sodium lauryl ether sulfate or SLES), or sodium myreth sulfate.

Further examples include perfluorobutanesulfonate, alkyl-aryl ether phosphates, alkyl ether phosphates, alkyl carboxylates such as sodium stearate, sodium lauroyl sarcosinate, carboxylate-based fluorosurfactants such as perfluorononanoate or perfluorooctanoate (PFOA or PFO).

The anionic surfactant can be present in the separation aid in any amount, such as from about 5 wt % to about 40 wt % based on the weight of the separation aid, such as from 10 wt % to 40 wt %, from 15 wt % to 40 wt %, from 5 wt % to 15 wt %, and the like.

Regarding the non-ionic surfactant, as used herein, a "non-ionic surfactant" is an organic compound that is amphiphilic and has no charge group at either terminal end group thereof, wherein the organic compound can lower the surface tension of a liquid, the interfacial tension between two liquids, or that between a liquid and a solid.

The non-ionic surfactant can be at least one alkoxylated castor oil. The non-ionic surfactant can be an ethoxylated sorbitan ester (polysorbate), an ethoxylated castor oil, a glyceride ethoxylate, an alcohol ethoxylate, an alkylphenol ethoxylate, a phenol ethoxylate, an amide ethoxylate, a fatty acid ethoxylate, a fatty amine ethoxylate, a fatty amide ethoxylate, a fatty mono or di-ethanolamide, an alkyl glycoside, a poloxamer, an ethoxylated fatty amide, and/or other non-ionic surfactants, which can be used in a single kind or any combination thereof.

The amount of the non-ionic surfactant included in the separation aid is an amount of from about 1 wt % to about 25% wt %, or from about 1 wt % to about 18 wt %, or from about 12 wt % to about 20 wt %, from about 1 wt % to about 10 wt %, from about 2 wt % to about 5 wt %, or other concentrations, based on total weight of the separation aid. As an option, at least two different non-ionic surfactants can be used in the separation aid of the present invention.

As further examples, the non-ionic surfactants can be a polysorbate or one or more nonionic polyethylene glycols, such as ethoxylate of carboxylic acids, ethoxylate of mono-, di- or triglycerides, ethoxylate of mono-, di- or triesters of sorbitan or ethoxylate of fatty alcohols. Other suitable non-ionic surfactants are mono-, di- or triglycerides based on fatty acids having 12-22 carbon atoms, or mono-, di- or triesters of sorbitan based on fatty acids having 12-22 carbon atoms. Commercial sources of the non-ionic surfactant which can be used in separation aids of the present invention include, for example, Lumisorb Polysorbates from Vantage Specialty Chemicals (Gurnee, Ill. USA) or Brij series polyoxyethylene vegetable-based fatty ethers available from Croda International (UK). The non-ionic surfactant may be at least one poloxamer. Poloxamers can be non-ionic tri-block copolymers that comprise a central block of a hydrophobic polyalkyleneoxide block, which is flanked on both sides with hydrophilic polyalkyleneoxide blocks. Poloxamers are commercially available that are food grade. A commercial source of poloxamers are, for example, PLURONIC® copolymers from BASF Corporation (Florham Park, N.J., U.S.A.).

The non-ionic surfactant can be an ethoxylated sorbitan ester. Ethoxylated sorbitan esters are also known as polysorbates. One kind of polysorbate, or two, three or more different kinds of polysorbates in combination, can be used as an option. The polysorbate may be polyoxyethylene sorbitan monolaurate, polyoxyethylene sorbitan monopalmitate, polyoxyethylene sorbitan monostearate, polyoxyethylene sorbitan monooleate, or other suitable or mono-, di- or triesters of sorbitan based on fatty acids having 12-22 carbon atoms, of a single kind or any combination thereof. The polysorbates can be commercially obtained as TWEEN or polysorbate series surfactant, such as polysorbate (80) (e.g., (TWEEN 80), polysorbate (20) (e.g., TWEEN 20), polysorbate (40) (e.g., TWEEN 40), or polysorbate 60 (e.g., TWEEN 60). TWEEN 80 is polyoxyethylene (20) sorbitan monooleate. Other commercial sources of the polysorbates which can be used in a chemical formulation of the present invention include, for example, Lumisorb Polysorbates from Vantage Specialty Chemicals (Gurnee, Ill. USA). The total amount of the polysorbate, if used as one of one or more non-ionic surfactants included in the chemical formulation of the present invention, can be in an amount or concentration of from about 5 wt % to about 65 wt %, or from about 15 wt % to about 60 wt %, or from about 25 wt % to about 60 wt %, or other concentrations, based on total weight of the separation aid.

As indicated, the non-ionic surfactant can be an alkoxylated castor oil. The alkoxylated castor oil can be ethoxylated castor oil. An ethoxylated castor oil can be prepared by ethoxylating castor oil, either naturally occurring or hydrogenated, under oxyalkylation conditions. As generally known, ethoxylation of the castor oil can be achieved by condensing a prescribed amount of ethylene oxide with the castor oil in the presence of a suitable catalyst. The ethoxylated castor oil can have from 20 to 90 moles of ethylene oxide (EO) per mole of castor oil, or from 30 to 80 moles of EO per mole of castor oil, or from 40 to 60 moles of EO per mole of castor oil, or other EO content. The ethoxylated castor oil can have a fatty acid end carbon number, such as from 10 to 20, 12 to 18, or 15 to 16, or other values. A commercial source of the ethoxylated castor oil can be T-Det C-40®, available from Harcros Chemicals Inc.

The non-ionic surfactant(s) can have a hydrophile-lipophile balance value (HLB value) of from about 2 to about 39, or an HLB value of from about 7 to about 25, or an HLB value of from about 10 to about 20, or an HLB value of from about 12 to about 18, or an HLB value of from about 14 to about 16, or an HLB value of about 15, or other values. When combinations of different surfactants are used, the weighted average of the individual surfactant components can be used to calculate the HLB of the combination. The HLB value can be calculated in a conventional manner. For example, the HLB value of a surface active agent can be calculated by dividing the molecular weight percent of the hydrophilic portion of the surface active agent by five. For example, a surfactant/wetting agent containing 20 mole % hydrophilic portion (total) would have an HLB value calculated to be 4 (i.e., 20/5=4). HLB values that exceed 20 are relative or comparative values. Additives with a low HLB are more lipid loving while those with a high HLB are more hydrophilic.

Regarding the organic solvent that is miscible in water, examples include alkylene glycols, alkyl alcohols (e.g., ethyl alcohol), and/or alkyl esters. One or two or more different organic solvents can be used or present in the separation aid. Preferably, the organic solvent is an acceptable food additive or considered GRAS by the FDA. The amount of the organic solvent(s) present in the separation aid can be from about 5 wt % to about 25 wt % such as from about 10 wt % to about 20 wt %, from about 15 wt % to about 25 wt % or any amounts within these ranges or below these ranges or above these ranges, where the wt % is based on the total weight of the separation aid.

Regarding the water present in the separation aid, the water can be any suitable water, such as municipal water, well water, spring water, distilled water, purified water, and the like. The amount of water present is any amount, such as from about 10 wt % to about 75 wt %, or from about 10 wt % to about 70 wt %, or from about 10 wt % to about 60 wt %, or from about 15 wt % to about 55 wt %, from about 20 wt % to about 50 wt %, or from about 40 wt % to about 75 wt %, or from about 40 wt % to about 70 wt %, or from about 50 wt % to about 75 wt %, or from about 40 wt % to about 60 wt %, from about 50 wt % to about 60 wt %, or any amounts within these ranges or below these ranges or above these ranges, where the wt % is based on the total weight of the separation aid.

Regarding the optional lecithin, the lecithin that can be used in the separation aid can be natural origin, modified origin, or synthetic. The lecithin which can be used in the present invention can be lecithin derived from any plant, animal or microbial source. Suitable lecithin starting materials are commercially available, and include available soybean lecithin and yolk lecithin products. Lecithin can be obtained from natural sources such as egg yolk, and plants such as soybean, maize, rapeseed, and the like where it is a by-product of vegetable oil refinement. Soybean oil is the largest source of commercial lecithin. The composition of commercial lecithin depends on the source, methods of preparation, and degree of purification, but in the most pure form it is comprised of mainly phosphatides. Commercial lecithin, for example, is a co-product of oil processing obtained during degumming step. For example, soybean lecithin is a complex mixture and comprises of phospholipids and triglycerides, with minor amounts of other constituents like phytoglycolipids, phytosterols, tocopherols and fatty acids. The major phospholipids present in vegetable lecithins are phosphatidylcholine, phosphatidylethanolamine and phosphatidylinositol. The egg yolk lecithin contains phosphatidylcholine and phosphatidylethanolamine as major phospholipids. Lecithin can be extracted chemically (using hexane) or mechanically from readily available sources such as soybeans. Lecithin has low solubility in water. In aqueous solution, its phospholipids can form either liposomes, bilayer sheets, micelles, or lamellar structures, depending on hydration and temperature. This results in a type of material that is usually classified as amphipathic. As used herein, "modified lecithin" refers to, but is not limited to, acetylation, hydroxylation, hydrogenation, hydrolysis products of lecithin, chlorination, bromination, iodination, halogenation, phosphorylation and sulfonation, as well as any other modification known to those in the art. Acetylated lecithins can be produced, for example, using a carboxylic acid anhydride like acetic anhydride for the acetylation of phospholipids from vegetable lecithins, such as shown in U.S. Pat. No. 3,301,881, which is incorporated herein by reference in its entirety. An enzymatic process can be used for the preparation of an acetylated phospholipid from vegetable lecithins such as soybean lecithin, rapeseed lecithin, and animal lecithins like egg yolk lecithin or pure phosphatidylethanolamine isolated from the above lecithins. Commercial lecithins can be acetylated, for example, by using vinyl acetate as acylating agent in presence of lipase from *Mucor miehei* having 1,3-position specificity as catalyst, such as shown in U.S. Pat. No. 6,403,344, which is incorporated herein by reference in its entirety. In acetylated lecithin, for example, acetylation occurs primarily on the amino group of phosphatidylethanolamine. The extent of acetylation on the modified lecithin, if used, can be partial or complete. The extent of acetylation on a modified lecithin can be, for example, from about 5% to 100%, or from about 10% to about 99%, or from about 15% to about 95%, or from about 20% to about 90%, or from about 25% to about 75%, or other values. Lecithin additionally contains a number of chemical functional groups that make it susceptible to a variety of chemical reactions. These groups include carbon-carbon double bonds, esters, phosphonate esters, amines and hydroxyl groups. Modification may also result in interesterified lecithin. Additionally, lecithins may be enzyme modified. As used herein, "phosphatides" (Phospholipids) refers to, but are not limited to, mixtures of phosphatidyl choline, phosphatidyl ethanolamine, phosphatidyl serine, phosphatidyl inositol, phosphatidic acid, N-acylphosphatidyl ethanolamine and other related minor constituents. Commercial sources of lecithin or modified lecithin which can be used in separation aids of the present invention include, for example, Solec HR 2B from Solae LLC (Memphis, Tenn. USA).

The lecithin, if used, can be present in an amount of from about 5 wt % to about 25 wt %, or from about 10 wt % to about 20 wt %, or from about 15 wt % to about 25 wt %, or any amounts within these ranges or below these ranges or above these ranges, where the wt % is based on the total weight of the separation aid.

As more specific examples, the separation aid can be or include a) at least one alkyl sulfosuccinate, and/or sulfated alcohol, and/or sulfated alcohol ethoxylate, b) ethoxylated castor oil, c) propylene glycol, and d) water.

As a more specific example, the separation aid can be or include a) at least one sulfosuccinate, and/or sulfated alcohol, and/or sulfated alcohol ethoxylate, b) ethoxylated castor oil, c) propylene glycol, d) ethyl alcohol, and e) water.

As another example, the separation aid can be or include a) at least one sulfosuccinate, sulfated alcohol, or sulfated alcohol ethoxylate, b) ethoxylated castor oil, c) propylene glycol, d) ethyl alcohol, e) water and f) at least one lecithin.

The separation aid can be or include from about 5 wt % to about 40 wt % of at least one sulfosuccinate, and/or sulfated alcohol, and/or sulfated alcohol ethoxylate, from about 1 wt % to about 25 wt % ethoxylated castor oil, from about 5 wt % to about 25 wt % propylene glycol, and from about 10 wt % to about 75 wt % water, based on the total weight of the separation aid.

The separation aid can be or include from about 5 wt % to about 40 wt % of at least one sulfosuccinate, and/or sulfated alcohol, and/or sulfated alcohol ethoxylate, from about 1 wt % to about 25 wt % ethoxylated castor oil, from about 5 wt % to about 25 wt % propylene glycol, from 1 wt % to about 15% ethyl alcohol, and from about 10 wt % to about 75 wt % water, based on the total weight of the separation aid.

The separation aid can be or include from about 5 wt % to about 40 wt % of at least one sulfosuccinate, and/or sulfated alcohol, and/or sulfated alcohol ethoxylate, from about 1 wt % to about 25 wt % ethoxylated castor oil, from about 5 wt % to about 25 wt % propylene glycol, from 1 wt % to about 15% ethyl alcohol, from about 10 wt % to about 75 wt % water, and from about 5 wt % to about 20 wt % of at least one lecithin, based on the total weight of the separation aid.

The separation aid can be formed by combining the ingredients, such as by mixing or blending or other techniques to combine wet and/or solid ingredients together.

The separation aid can be used, for example, in a method of recovering distillers grains from a stillage byproduct resulting from the production of ethanol from corn or other plant and/or food material, such as by using a dry milling technique, such as described in U.S. Pat. No. 5,250,182, which is incorporated herein in its entirety by reference. The stillage byproduct can be whole stillage, thin stillage, or syrup.

Figure 1:
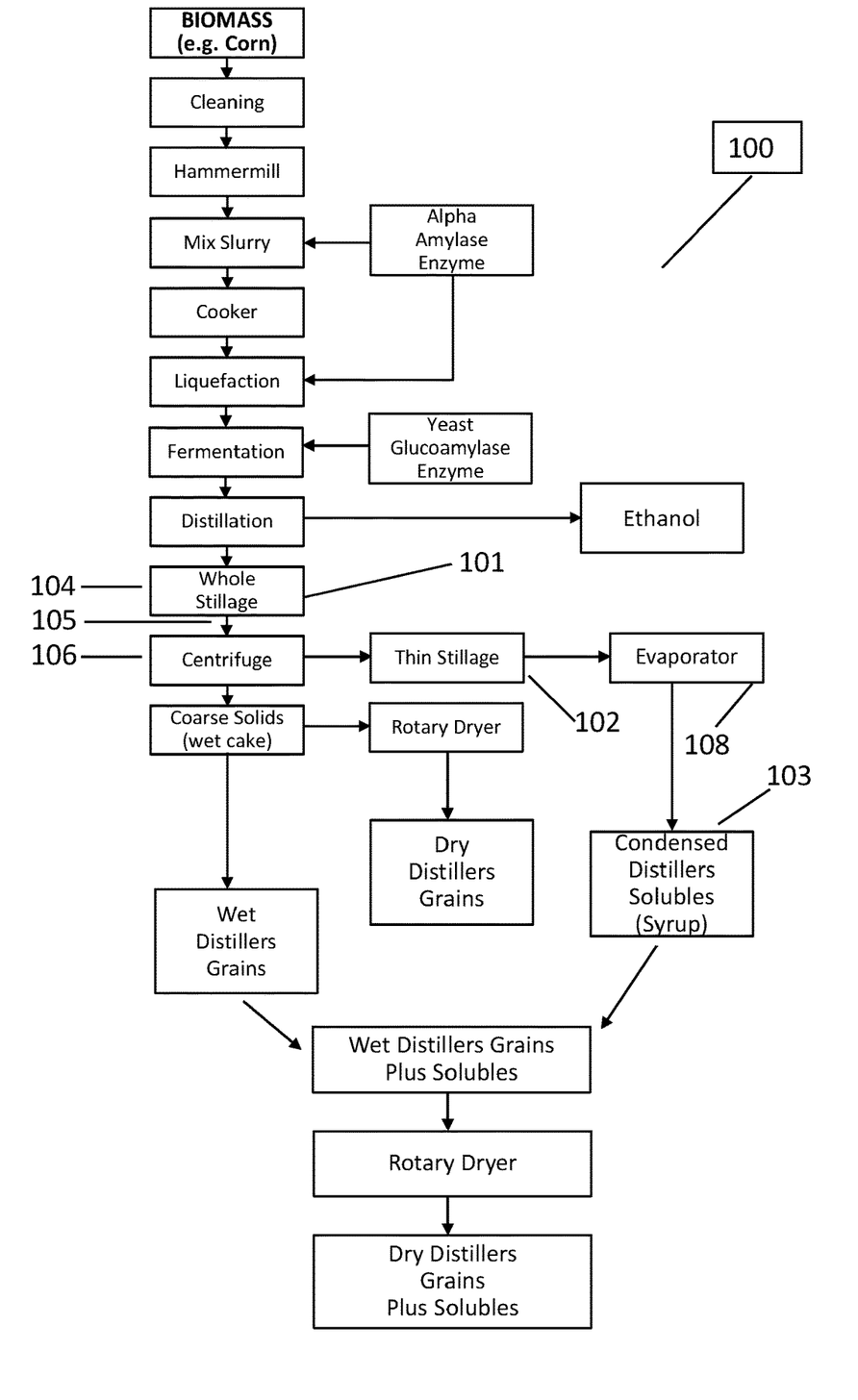
FIG. 1 is a process flow diagram of one example of ethanol production from corn (or other fermentable starch-containing biomass) that includes WDG, DDG and/or DDGS recovery from stillage treated with a separation aid.

Referring to FIG. 1, a process 100 is shown for the production of ethanol biofuel and byproducts, such as from corn or other food or plant material. Several process byproducts 101, 102, 103 are identified in this FIGURE for purposes of exemplifying various types of "stillage." As shown in FIG. 1, following distillation, the whole stillage is first treated with the separation aid by introducing the separation aid at 104 (before the centrifuge) and/or as a stream 105 as the stillage is transferred to the centrifuge and/or into the centrifuge 106 before centrifuging starts or as it starts. Then the treated stillage is separated by centrifuge, such as a decanter centrifuge, into wet grains and thin stillage. Evaporator 108 can concentrate thin stillage into syrup by evaporation, and the syrup can be combined with wet grains to produce distiller grains and solubles (DGS), or can be dried to produce distiller dried grains and solubles (DDGS), or both. As indicated herein, the separation aid is added to the stillage, which preferably is the whole stillage 101. Any means to add the separation aid to the stillage can be used as long as the separation aid is adequately mixed with the stillage prior to conducting the centrifuging of the whole stillage. Corn can be the biomass material in FIG. 1 for sake of illustration, and other biomass materials can be used, such as other fermentable starch-containing biomass materials.

The centrifuge can be, for example a decanter centrifuge, a horizontal centrifugal solid bowl decanter, a disk stack centrifuge, a hermetically sealed centrifuge, or other type of centrifuge or gravity separator.

For purposes of the present invention, a centrifuge or a step of centrifuging is referred to throughout, but it is to be understood that any mechanical separation step can be utilized in lieu of centrifuging such as, but not limited to, decanting or other solid-liquid extraction devices.

In the method of the present invention, the liquid fraction is separated during centrifuging from the solids that ultimately form the wet cake or WDG and then the DDG. The liquid portion can be treated to recover oil and fats as a separate stream.

The separation aid can be added to the stillage (e.g., whole stillage) as indicated in an amount so as to be present in a ppm range of from about 10 ppm to 1,000 ppm in the stillage, such as the whole stillage. This ppm range can be from about 10 ppm to 49 ppm.

The separation aid can be added to the stillage utilizing a side stream. The separation aid can be added directly into a centrifuge and present with the stillage which is whole stillage, and prior to conducting any actual centrifuging. The separation aid can be mixed with the stillage prior to entering a centrifuge used for the centrifuging.

The stillage, such as the whole stillage can have a solids content of from 5 wt % to 80 wt % (based on the weight of the stillage) when the separation aid is added to whole stillage.

In the present invention, the coarse solids or distillers' grains (e.g., wet distillers' grain) recovered after the centrifuging and then optionally dried to obtain DDG can have an oil content of below 15 wt % by total weight of the dried distillers' grains, for instance, below 7 wt %, or from about 3 wt % to about 6 wt % or about 3 wt % to 6 wt %, by total weight of said dried distillers' grains. The oil content mentioned here can include "fat" that is present as a liquid due to the temperature of the wet cake, WDG, DDG and/or DDGS being high enough to liquefy the fat.

The ppm values indicated herein are based on weight/weight values.

As an option, the separation aid can have less than 1 wt % polysorbate, such as 0 wt % or from 0 wt % to 0.9 wt % or from 0.1 wt % to 0.5 wt %, based on the total weight of the separation aid.

As a separate option, the separation aid can have less than 1 wt % mineral oil and vegetable oil, such as 0 wt % or from 0 wt % to 0.9 wt % or from 0.1 wt % to 0.5 wt %, based on the total weight of the separation aid.

The separation aid can be formulated as very low in aromatic content or aromatic free. The separation aid can be formulated, for example, as comprising less than 1 wt % aromatic compounds, or less than 0.5 wt % aromatics, or less than 0.1 wt % aromatics, or 0 wt % aromatics.

The separation aid can be formulated as being low in alcohol content. The separation aid can be formulated, for example, as comprising from about 0.1 wt % to about 15 wt % alcohol, or from about 0.5 wt % to about 5 wt % alcohol or from about 1 wt % to about 2 wt % alcohol. The reference to alcohol can be to ethyl alcohol alone or to a combination of alcohols.

The separation aid can be a food-grade or GRAS approved composition or mixture.

In the present invention, as an option, the separation aid has less than 1 wt % oil (e.g., 0 wt %, less than 0.01 wt %, less than 0.05 wt %, less than 0.1 wt %, less than 0.5 wt %) based on the total weight of the separation aid. This category of oil is mineral oil, triglyceride vegetable oil, hydrocarbon oil, or any combination thereof. The mineral oil can be, for example, white mineral oil or mineral seal oil. Examples of the mineral oil can be the atmospheric residue oil obtained in the distillation of crude oil, vacuum gas oil, and vacuum residue oil obtained by vacuum distillation of the atmospheric residue oil, their hydrotreated oils, pyrolysis oils, and or their mixtures. Among these mineral oils, the atmospheric residue oil, vacuum residue oil, and their hydrotreated products or pyrolysis products are referred to as residue oils in the present invention. The triglyceride vegetable oil can be, for example, triglyceride corn oil. The hydrocarbon oil can be, for example, white mineral oil, or any combinations thereof. Commercial sources of the oil which can be used in separation aids of the present invention include, for example, Clarion White Mineral Oil 70, CITGO Petroleum (Houston, USA).

The separation aid composition can contain additional optional additives. For example, the separation aid can contain particulate material such as silica, talc, and/or bentonite clay. The material can be organic or inorganic. The preferred types of particular material can be fumed or precipitated silica. The silica can be hydrophobic or hydrophilic. If used, the one or more additional additives, such as silica, can be contained in the separation aid in an amount, for example, of from about 1 wt % to 15 wt % or other amounts or ranges.

The present invention will be further clarified by the following examples, which are intended to be only exemplary of the present invention. Unless indicated otherwise, all amounts, percentages, ratios and the like used herein are by weight.

EXAMPLES

Example 1

Bench testing was performed on corn oil to determine the effect of various inventive compositions and one comparative by measuring interfacial tension (IFT).

TABLE 1

| Product composition information | | | | |
|---|---|---|---|---|
| Components | XP16-A | XP16-B | XP16-C | XP16-D |
| Tween 80 | 50 | 100 | / | / |
| DOSS 75 | 15 | / | 30 | 9.2 |
| Solae HR2B | / | / | / | 14.3 |
| Castor Oil 40 | 1.5 | / | 3 | 17.4 |
| Propylene Glycol | 15 | / | 30 | 9.2 |
| Water | 18.5 | / | 37 | 49.9 |

The IFT was measured using a KRUSS spinning drop tensiometer at 87.7±0.3° C. For this, 1-5 μL of corn oil was injected in to the capillary tube that is pre-filled with 500 ppm of separation aid (XP16-A-D) in a simulated supernatant of whole stillage. The capillary tube was then spun so that an oil drop expanded several times its diameter. IFT measurements were recorded in every 1 min for total of 10 mins.

It was observed that XP16-D generated lowest IFT of 0.41 mN/m, while XP16-C had the highest IFT of 1.17 mN/m. XP16-A (0.52 mN/m) and XP16-B (0.65 mN/m) show slightly higher IFT than XP16-D but still twice as low IFT than XP16-C. A lower IFT suggests that the product has better detergency characteristics and thus will be more effective for whole stillage treatment application.

Example 2

Additional testing was performed, wherein the compositions of Table 1 were trialed for whole stillage treatment at an ethanol plant. Whole stillage, wet distillers grain (WDG), and thin stillage samples were collected before and after treatment and were analyzed using high performance liquid chromatography (HPLC). Results showed, first, that XP16-D, having the lowest IFT, reduced the oil/fat content in the dried wet cake by more than 1 wt %, and second, increased the thin stillage oil content by 0.2 wt %. XP-16-A and XP-16-B reduced the oil/fat content of dried wet cake by about 0.6 wt % and XP-16-C reduced the DDG oil/fat content by about 0.1 wt %.

The present invention includes the following aspects/embodiments/features in any order and/or in any combination:

1. A method to lower oil content in distillers grains from a fermentation process, comprising
adding at least one separation aid to stillage that contains oil emulsion, to form a treated stillage prior to centrifuging said stillage, and
centrifuging said treated stillage in at least one centrifuge to separate at least a portion of said oil emulsion from said treated stillage to obtain said oil emulsion separated from dried distillers' grain, wherein said separation aid comprises at least one anionic surfactant, at least one non-ionic surfactant, at least one organic solvent that is miscible in water, and water, and optionally at least one lecithin.

2. The method of any preceding or following embodiment/feature/aspect, wherein said separation aid comprises at least one sulfocarboxylate, sulfated alcohol, or sulfated alcohol ethoxylate, ethoxylated castor oil, propylene glycol, and water.

3. The method of any preceding or following embodiment/feature/aspect, wherein said separation aid comprises at least one sulfocarboxylate, sulfated alcohol, or sulfated alcohol ethoxylate, ethoxylated castor oil, propylene glycol, ethyl alcohol, water, and at least one lecithin.

4. The method of any preceding or following embodiment/feature/aspect, wherein said separation aid comprises from about 5 wt % to about 40 wt % of at least one sulfocarboxylate, sulfated alcohol, or sulfated alcohol ethoxylate, from about 1 wt % to about 25 wt % ethoxylated castor oil, from about 5 wt % to about 25 wt % propylene glycol, and from about 10 wt % to about 75 wt % water.

5. The method of any preceding or following embodiment/feature/aspect, wherein said separation aid comprises from about 5 wt % to about 40 wt % of at least one sulfocarboxylate, sulfated alcohol, or sulfated alcohol ethoxylate, from about 1 wt % to about 25 wt % ethoxylated castor oil, from about 5 wt % to about 25 wt % propylene glycol, from about 10 wt % to about 75 wt % water, from 1 wt % to about 15% ethyl alcohol, and from about 5 wt % to about 20 wt % of at least one lecithin.

6. The method of any preceding or following embodiment/feature/aspect, wherein said separation aid comprises from about 5 wt % to about 15 wt % of at least one sulfocarboxylate, sulfated alcohol, or sulfated alcohol ethoxylate, from about 10 wt % to about 25 wt % ethoxylated castor oil, from about 5 wt % to about 15 wt % propylene glycol, from about 40 wt % to about 75 wt % water, from 1 wt % to about 15% ethyl alcohol, and from about 5 wt % to about 20 wt % of at least one lecithin.

7. The method of any preceding or following embodiment/feature/aspect, wherein said at least one lecithin is present and is soy lecithin or soybean lecithin.

8. The method of any preceding or following embodiment/feature/aspect, wherein said sulfocarboxylate is sodium dioctyl sulfosuccinate.

9. The method of any preceding or following embodiment/feature/aspect, wherein the separation aid comprises less than 1 wt % polysorbate.

10. The method of any preceding or following embodiment/feature/aspect, wherein the separation aid comprises less than 1 wt % mineral oil and vegetable oil.

11. The method of any preceding or following embodiment/feature/aspect, wherein said stillage is whole stillage, and said adding occurs in said whole stillage prior to conducting said centrifuging.

12. The method of any preceding or following embodiment/feature/aspect, wherein said distillers grains is recovered as a separate stream.

13. The method of any preceding or following embodiment/feature/aspect, wherein said separation aid is added in an amount to be present in a ppm range of from about 10 ppm to 1,000 ppm.

14. The method of any preceding or following embodiment/feature/aspect, wherein said separation aid is added in an amount to be present in a ppm range of from about 10 ppm to 49 ppm.

15. The method of any preceding or following embodiment/feature/aspect, wherein said lecithin is present and is an acetylated lecithin.

16. The method of any preceding or following embodiment/feature/aspect, wherein said separation aid is added to said stillage utilizing a side stream.

17. The method of any preceding or following embodiment/feature/aspect, wherein said separation aid is added directly into a centrifuge, and present with said stillage that is whole stillage, and prior to conducting said centrifuging.

18. The method of any preceding or following embodiment/feature/aspect, wherein said separation aid is mixed with said stillage prior to entering a centrifuge used for said centrifuging.

19. The method of any preceding or following embodiment/feature/aspect, wherein said stillage is whole stillage and has a solids content of from 5 wt % to 20 wt % when said separation aid is added to said whole stillage.

20. The method of any preceding or following embodiment/feature/aspect, wherein said distillers' grains is recovered after said centrifuging and has an oil and fat content of below 15 wt % by total weight of said distillers' grains based on a dry basis.

21. The method of any preceding or following embodiment/feature/aspect, wherein said distillers' grains is recovered after said centrifuging and has an oil content of below 7 wt % by total weight of said distillers' grains on a dry basis.

22. The method of any preceding or following embodiment/feature/aspect, wherein said distillers' grains is recovered after said centrifuging and has an oil content of from about 3 wt % to about 6 wt % by total weight of said distillers' grains on a dry basis.

23. The method of any preceding or following embodiment/feature/aspect, wherein said stillage is a byproduct from a corn fermentation process.

24. The method of any preceding or following embodiment/feature/aspect, wherein said stillage is a byproduct from a sugar cane fermentation process.

25. The method of any preceding or following embodiment/feature/aspect, wherein said separation aid comprises less than 1 wt % aromatic compounds.

26. The method of any preceding or following embodiment/feature/aspect, wherein said separation aid is a food-grade or GRAS approved composition or mixture.

27. The method of any preceding or following embodiment/feature/aspect, wherein said separation aid further comprises silica.

28. An separation aid composition comprising
   a) from 5 wt % to 40 wt % of at least one anionic surfactant;
   b) from 1 wt % to 25 wt % of at least one non-ionic surfactant;
   c) from 5 wt % to 25 wt % of at least one organic solvent that is miscible in water;
   d) water; and
   e) optionally at least one lecithin.

29. A treated stillage comprising the separation aid of any preceding or following embodiment/feature/aspect and stillage wherein said separation aid is present in an amount of from about 10 ppm to about 1,000 ppm.

30. The treated stillage of any preceding or following embodiment/feature/aspect, wherein said solids content of said treated stillage is from 5 wt % to 40 wt %.

31. The separation aid of any preceding or following embodiment/feature/aspect, wherein
   said anionic surfactant is at least one sulfocarboxylate, sulfated alcohol, or sulfated alcohol ethoxylate;
   said non-ionic surfactant is ethoxylated castor oil; and
   said organic solvents are propylene glycol and ethyl alcohol.

32. The separation aid of any preceding or following embodiment/feature/aspect, wherein said lecithin is present in an amount of from about 5 wt % to about 20 wt %.

33. The method of any preceding or following embodiment/feature/aspect, wherein said non-ionic surfactant comprises at least one polysorbate.

34. The method of any preceding or following embodiment/feature/aspect, wherein said non-ionic surfactant comprises at least one polysorbate in an amount of from about 5 wt % to about 65% wt % based on total weight of the separation aid.

35. The method of any preceding or following embodiment/feature/aspect, wherein said non-ionic surfactant comprises at least two different non-ionic surfactants, wherein one of said non-ionic surfactants is a polysorbate.

36. The separation aid of any preceding or following embodiment/feature/aspect, wherein said non-ionic surfactant comprises at least one polysorbate.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method to lower oil content in distillers grains from a fermentation process, comprising
   adding at least one separation aid to stillage that contains suspended solids and oil emulsion, to form a treated stillage prior to centrifuging said stillage, and
   centrifuging said treated stillage in at least one centrifuge to separate at least a portion of said oil emulsion from said treated stillage to obtain said oil emulsion separated from distillers' grain, wherein said separation aid comprises at least one anionic surfactant, at least one non-ionic surfactant, at least one organic solvent that is miscible in water, and water, and optionally at least one lecithin, wherein the separation aid does not break the oil emulsion when present together in the treated stillage.

2. The method of claim 1, wherein said separation aid comprises a) at least one sulfocarboxylate, sulfated alcohol, or sulfated alcohol ethoxylate, b) ethoxylated castor oil, c) propylene glycol, and d) water.

3. The method of claim 1, wherein said separation aid comprises a) at least one sulfocarboxylate, sulfated alcohol or sulfated alcohol ethoxylate, b) ethoxylated castor oil, c) propylene glycol, d) ethanol, e) water, and f) at least one lecithin.

4. The method of claim 1, wherein said separation aid comprises from about 5 wt % to about 40 wt % of at least one sulfated alcohol or sulfated alcohol ethoxylate, from about 1 wt % to about 25 wt % ethoxylated castor oil, from about 5 wt % to about 25 wt % propylene glycol, and from about 10 wt % to about 75 wt % water.

5. The method of claim 1, wherein said separation aid comprises from about 5 wt % to about 40 wt % of at least one sulfocarboxylate, sulfated alcohol or sulfated alcohol ethoxylate, from about 1 wt % to about 25 wt % ethoxylated castor oil, from about 5 wt % to about 25 wt % propylene glycol, from about 10 wt % to about 75 wt % water, and from about 5 wt % to about 20 wt % of at least one lecithin.

6. The method of claim 1, wherein said separation aid comprises from about 5 wt % to about 15 wt % of at least one sulfocarboxylate, sulfated alcohol or sulfated alcohol ethoxylate, from about 10 wt % to about 25 wt % ethoxylated castor oil, from about 5 wt % to about 15 wt % propylene glycol, from about 40 wt % to about 75 wt % water, from 1 wt % to about 15% ethyl alcohol, and from about 5 wt % to about 20 wt % of at least one lecithin.

7. The method of claim 1, wherein said at least one lecithin is present and is soy lecithin or soybean lecithin.

8. The method of claim 2, wherein said sulfocarboxylate is sodium dioctyl sulfosuccinate.

9. The method of claim 1, wherein the separation aid comprises less than 1 wt % polysorbate.

10. The method of claim 1, wherein the separation aid comprises less than 1 wt % mineral oil and vegetable oil.

11. The method of claim 1, wherein said stillage is whole stillage, and said adding occurs in said whole stillage prior to conducting said centrifuging.

12. The method of claim 1, wherein said distillers grains is recovered as a separate stream.

13. The method of claim 1, wherein said separation aid is added in an amount to be present in a ppm range of from about 10 ppm to 1,000 ppm.

14. The method of claim 1, wherein said separation aid is added in an amount to be present in a ppm range of from about 10 ppm to 49 ppm.

15. The method of claim 1, wherein said lecithin is present and is an acetylated lecithin.

16. The method of claim 1, wherein said separation aid is added to said stillage utilizing a side stream.

17. The method of claim 1, wherein said separation aid is added directly into a centrifuge, and present with said stillage that is whole stillage, and prior to conducting said centrifuging.

18. The method of claim 1, wherein said separation aid is mixed with said stillage prior to entering a centrifuge used for said centrifuging.

19. The method of claim 1, wherein said stillage is whole stillage and has a solids content of from 5 wt % to 20 wt % when said separation aid is added to said whole stillage.

20. The method of claim 1, wherein said distillers' grains is recovered after said centrifuging and has an oil content of below 15 wt % by total weight of said distillers' grains on a dry basis.

21. The method of claim 1, wherein said distillers' grains is recovered after said centrifuging and has an oil content of below 7 wt % by total weight of said distillers' grains on a dry basis.

22. The method of claim 1, wherein said distillers' grains is recovered after said centrifuging and has an oil content of from about 3 wt % to about 6 wt % by total weight of said distillers' grains on a dry basis.

23. The method of claim 1, wherein said stillage is a by product from a corn fermentation process.

24. The method of claim 1, wherein said stillage is a by product from a sugar cane fermentation process.

25. The method of claim 1, wherein said separation aid comprises less than 1 wt % aromatic compounds.

26. The method of claim 1, wherein said separation aid is a food-grade or GRAS approved composition or mixture.

27. The method of claim 1, wherein said separation aid further comprises silica, talc, or bentonite clay.

28. The method of claim 1, wherein said non-ionic surfactant comprises at least one polysorbate.

29. The method of claim 1, wherein said non-ionic surfactant comprises at least one polysorbate in an amount of from about 5 wt % to about 65% wt % based on total weight of the separation aid.

30. The method of claim 1, wherein said non-ionic surfactant comprises at least two different non-ionic surfactants, wherein one of said non-ionic surfactants is a polysorbate.

* * * * *